United States Patent
Protasiewicz et al.

(10) Patent No.: US 10,166,342 B2
(45) Date of Patent: Jan. 1, 2019

(54) RECOIL REDUCING NEEDLE SHIELDS

(71) Applicant: West Pharmaceutical Services, Inc., Exton, PA (US)

(72) Inventors: Raymond Protasiewicz, Whippany, NJ (US); Brian Costello, Whitehouse Station, NJ (US); Christopher Evans, Long Valley, NJ (US); Christopher Gieda, Long Valley, NJ (US)

(73) Assignee: West Pharmaceutical Services, Inc., Exton, PA (US)

( * ) Notice: Subject to any disclaimer, the term of this patent is extended or adjusted under 35 U.S.C. 154(b) by 122 days.

(21) Appl. No.: 14/980,908

(22) Filed: Dec. 28, 2015

(65) Prior Publication Data

US 2016/0206829 A1    Jul. 21, 2016

Related U.S. Application Data

(60) Provisional application No. 62/105,872, filed on Jan. 21, 2015.

(51) Int. Cl.
*A61M 5/32* (2006.01)

(52) U.S. Cl.
CPC ........ *A61M 5/3202* (2013.01); *A61M 5/3204* (2013.01)

(58) Field of Classification Search
CPC .. A61M 5/3202; A61M 5/3204; A61M 5/321; A61M 5/3213; A61M 2005/3109;
(Continued)

(56) References Cited

U.S. PATENT DOCUMENTS 3,703,975 A * 11/1972 Wittemer ............. B65D 50/067
                                                    215/211
4,430,082 A *  2/1984 Schwabacher ...... A61M 5/3202
                                                    604/263
(Continued)

FOREIGN PATENT DOCUMENTS

WO    2014031521 A1    2/2014

OTHER PUBLICATIONS

Extended European Search Report dated Jun. 22, 2016 in EP Application No. 16151738.8.

*Primary Examiner* — Emily Schmidt
*Assistant Examiner* — Alexandra Lalonde
(74) *Attorney, Agent, or Firm* — Panitch Schwarze Belisario & Nadel LLP

(57) ABSTRACT

A recoil reducing needle shield for covering a drug container with a needle includes an outer shell, including an upper portion, a lower portion, and at least one flexible interface positioned therebetween, defining a fulcrum. Radially inward flexing of the upper portion causes radially outward flexing of the lower portion about the flexible interface. An inner cover includes an open proximal end, a closed distal end, and a needle cavity defined therein for receiving a portion of the drug container including the needle. At least a portion of the inner cover is disposed within the outer shell. The open proximal end of the inner cover is coupled to the lower portion of the outer shell, such that radially outward flexing of the lower portion stretches the open proximal end of the inner cover, thereby reducing an initial pull-off force required to remove the needle shield from the drug container.

11 Claims, 15 Drawing Sheets

(58) Field of Classification Search
CPC .. A61M 2005/3118; A61M 2005/3215; A61M 2005/312; A61M 5/3245; A61M 2005/3246; A61M 2005/3256; B65D 50/045; B65D 50/046; B65D 50/00
See application file for complete search history.

(56) References Cited

U.S. PATENT DOCUMENTS

| | | | |
|---|---|---|---|
| 4,480,762 A * | 11/1984 | Thomas | B65D 50/045 215/216 |
| 4,921,489 A | 5/1990 | Frizzell | |
| 4,981,476 A * | 1/1991 | Aichlmayr | A61M 5/3213 206/365 |
| 5,143,414 A | 9/1992 | Rosellini | |
| 5,433,330 A * | 7/1995 | Yatsko | A61J 1/1406 215/247 |
| 5,979,680 A * | 11/1999 | Farside | B65D 50/046 215/211 |
| 2007/0250016 A1 * | 10/2007 | Pech | A61M 5/3202 604/198 |
| 2013/0289489 A1 | 10/2013 | Evans et al. | |

* cited by examiner

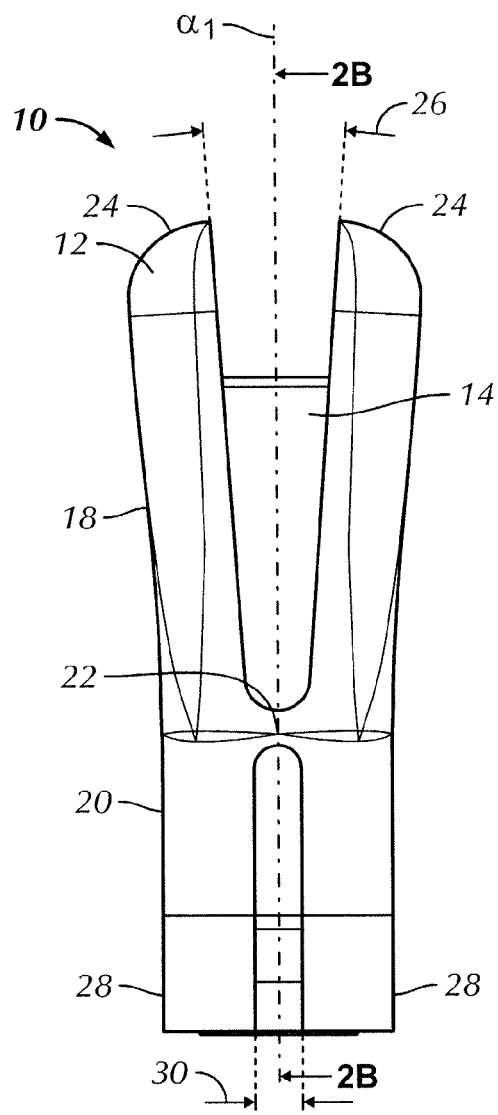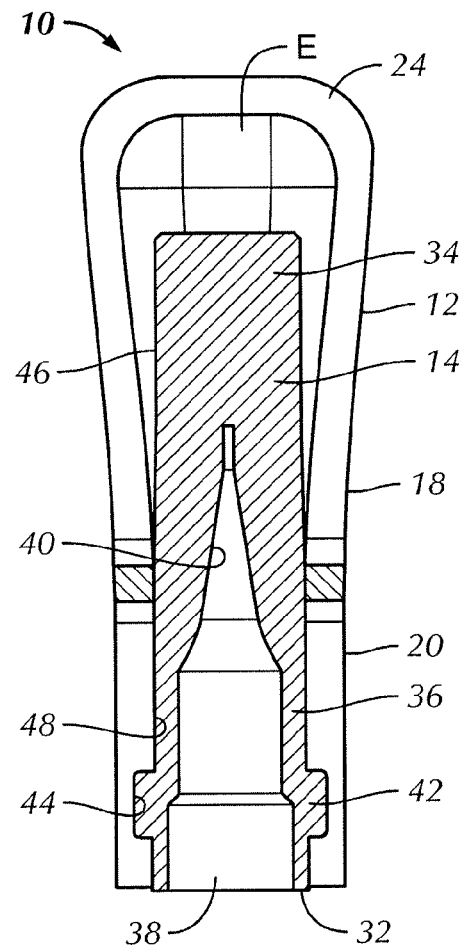
FIG. 2A
FIG. 2B

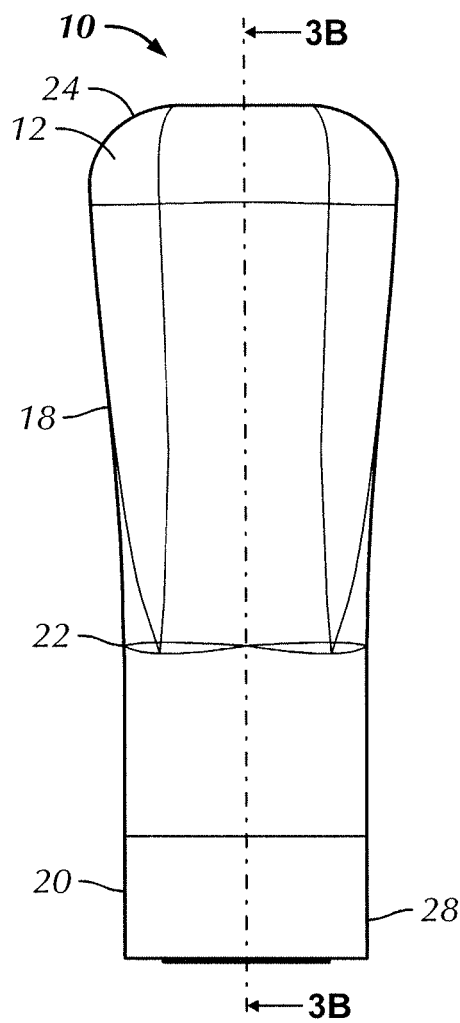
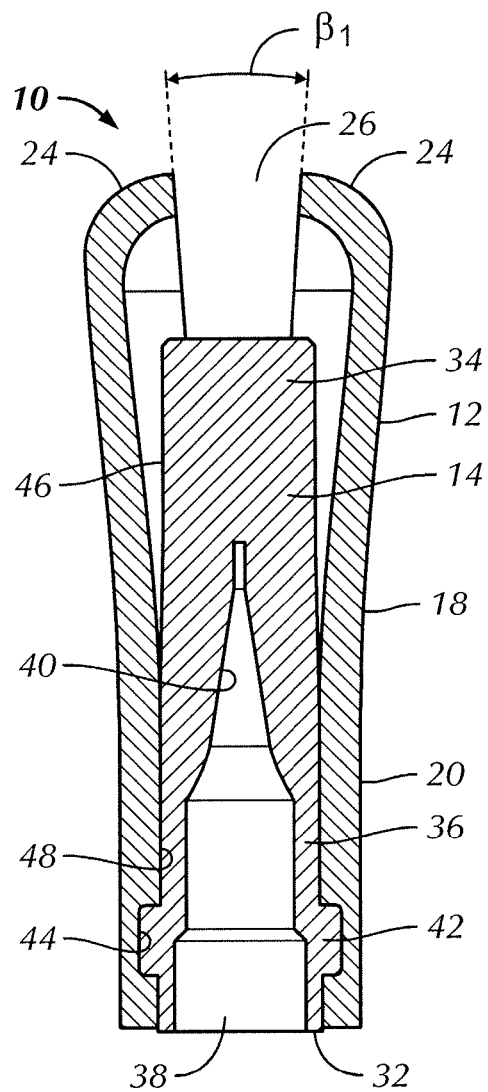
FIG. 3A
FIG. 3B

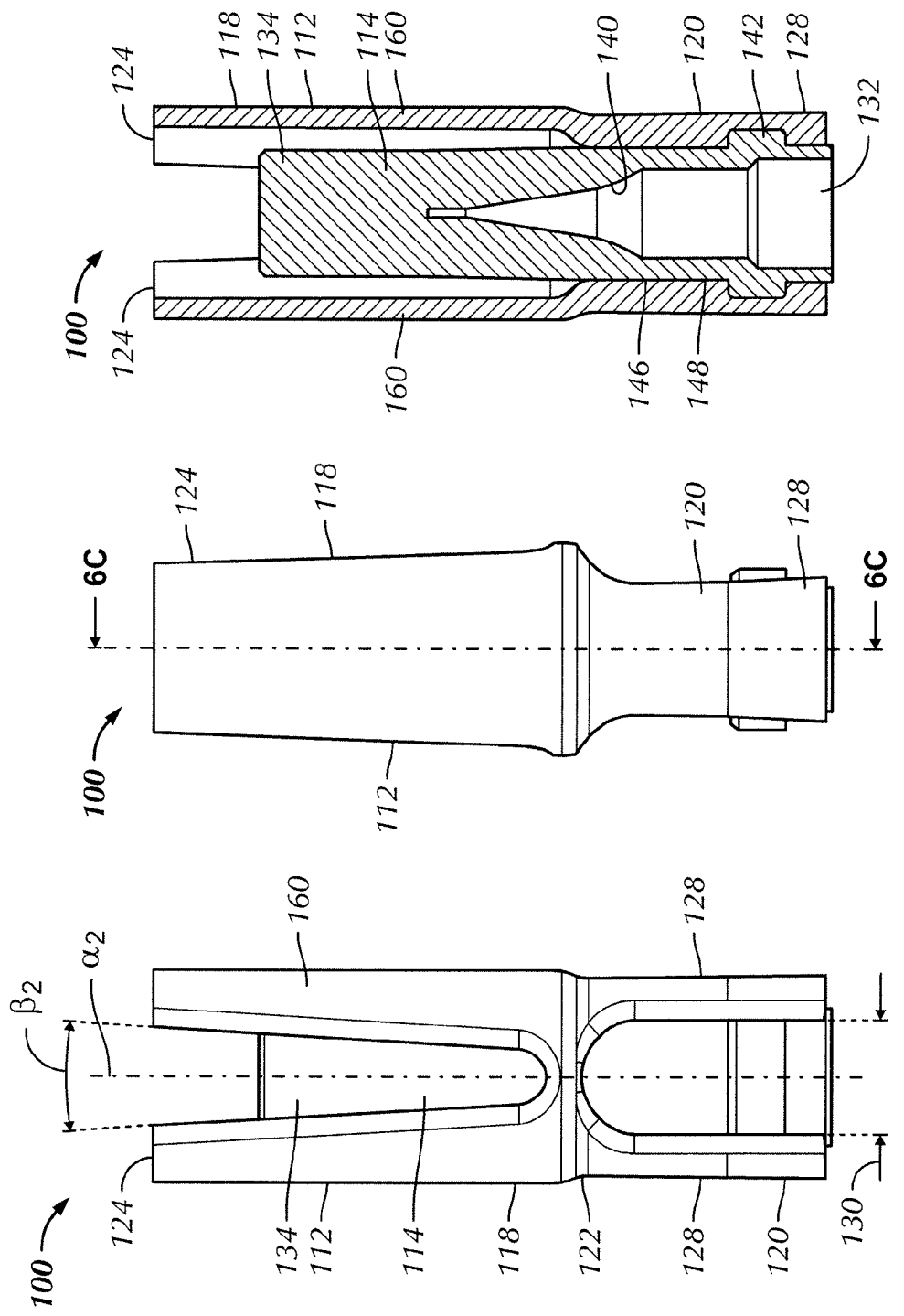

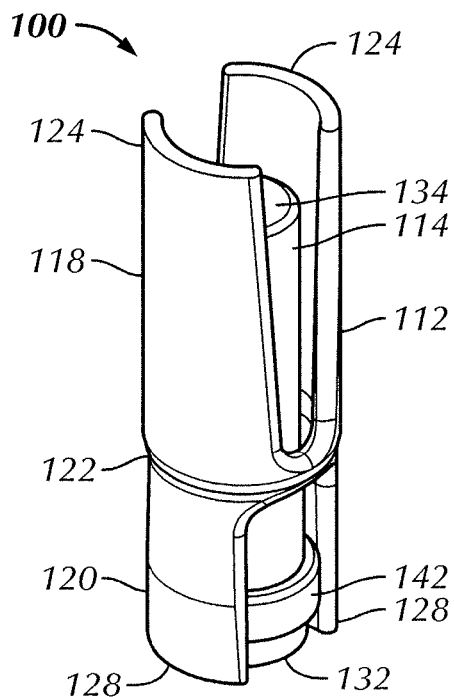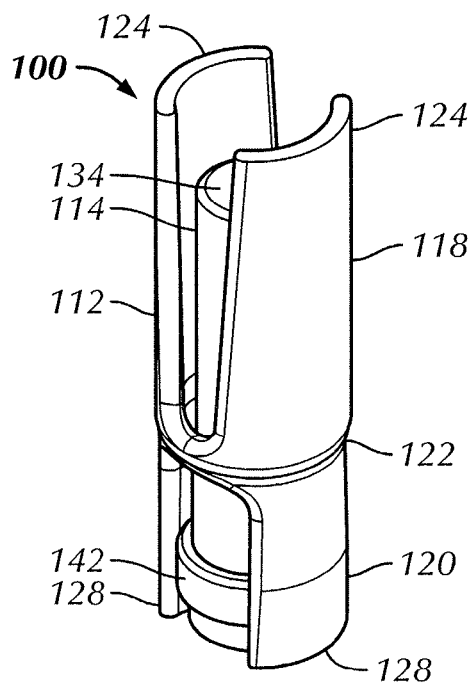
FIG. 7A  FIG. 7B
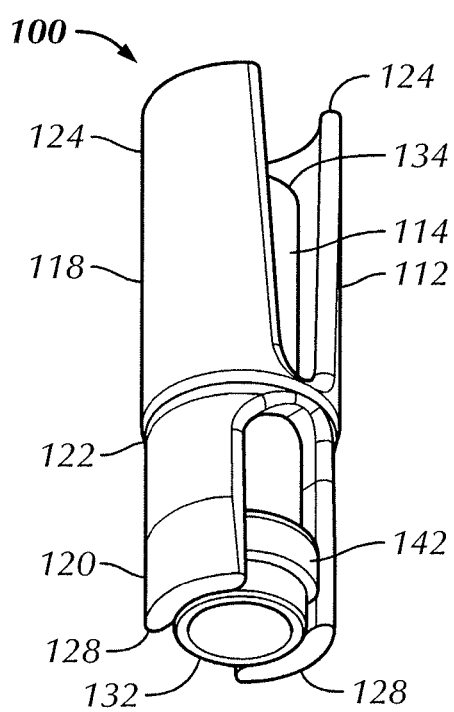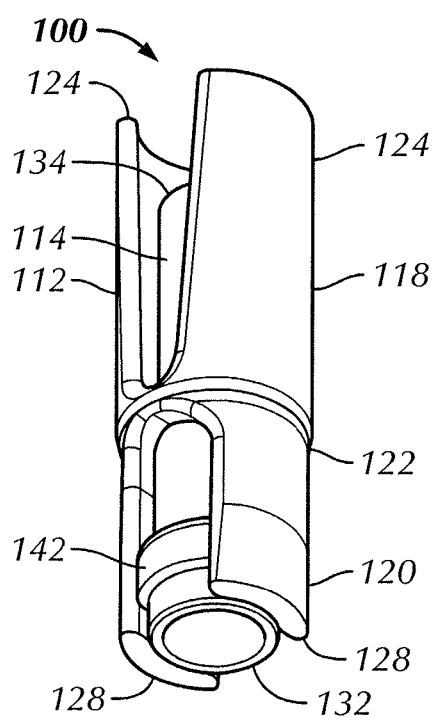
FIG. 7C  FIG. 7D

RECOIL REDUCING NEEDLE SHIELDS

CROSS REFERENCE TO RELATED APPLICATIONS

This application claims priority to U.S. Provisional Patent Application No. 62/105,872, filed on Jan. 21, 2015, entitled "Recoil Preventing Needle Shields," the entire contents of which are incorporated by reference herein.

BACKGROUND OF THE INVENTION

The present invention relates to needle shields, and particularly needle shields configured to reduce or prevent recoil from occurring after removal of a needle shield from a needle holder, e.g. a syringe.

Needle shield removal is a known contributor to accidental needle stick injuries, particularly in the clinical work place. Injuries that occur after needle shield removal are due, in part, to the phenomena of "recoil." Recoil can occur when a user tries to overcome the initial pull off force required to remove a needle shield from a syringe. Upon the abrupt release of a needle shield from the syringe, a user may compensate for the spike in the initial break away force of the needle shield from the syringe by pulling back slightly. As the user "pulls back," the hand grasping the needle shield will involuntarily recoil or bounce back toward the uncovered needle in the other hand, resulting in an accidental needle stick injury.

Despite efforts to prevent recoil from occurring, needle stick injuries still occur. Accordingly, there is a need for improved needle shields that reduce or prevent recoil and lessen the potential for accidental needle stick injuries in a cost effective and economical manner.

BRIEF SUMMARY OF THE INVENTION

Briefly stated, one aspect of the present invention is directed to a recoil reducing needle shield for covering a drug container with a needle. The needle shield comprises an outer shell, including an upper portion, a lower portion, and at least one flexible interface positioned therebetween and defining a fulcrum therebetween, such that radially inward flexing of the upper portion causes radially outward flexing of the lower portion about the at least one flexible interface. An inner cover includes an open proximal end, a closed distal end, and a needle cavity defined therein for receiving a portion of the drug container including the needle. At least a portion of the inner cover is disposed within the outer shell. The open proximal end of the inner cover is coupled to at least a portion of the lower portion of the outer shell, such that radially outward flexing of the lower portion stretches the open proximal end of the inner cover, thereby reducing an initial pull-off force required to remove the needle shield from the drug container.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings preferred embodiments of a needle shield which are presently preferred. It should be understood, however, that the invention is not limited to the precise arrangements and instrumentalities shown. In the drawings:

FIG. 2A is a front elevational view of the recoil preventing needle shield of FIG. 1;

FIG. 2B is a cross-sectional elevational view of the needle shield of FIG. 2A, taken along sectional line 2B-2B;

FIG. 3A is a side elevational view of the needle shield of FIG. 2A;

FIG. 3B is a cross-sectional elevational view of the needle shield of FIG. 3A, taken along sectional line 3B-3B;

FIG. 6A is a front elevational view of a second embodiment of a recoil preventing needle shield;

FIG. 6B is a side elevational view of the needle shield of FIG. 6A;

FIG. 6C is a cross-sectional elevational view of the needle shield of FIG. 6A, taken along sectional line 6C-6C of FIG. 6B;

FIG. 7A is an upper front, right perspective view of the needle shield of FIG. 6A;

FIG. 7B is an upper front, left perspective view of the needle shield of FIG. 6A;

FIG. 7C is a lower front, right perspective view of the needle shield of FIG. 6A;

FIG. 7D is a lower front, left perspective view of the needle shield of FIG. 6A;

DETAILED DESCRIPTION OF THE INVENTION

Figure 1A:
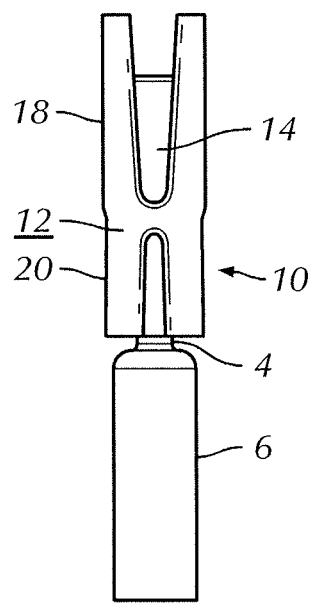
FIG. 1A is a front elevational view of a first embodiment of a recoil preventing needle shield in a relaxed state, positioned on a syringe before removal by a user.

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the needle shield, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import. It should also be noted that the terms "first," "second," "third" and the like may be used herein to modify various elements. These modifiers do not imply a spatial, sequential, or hierarchical order to the modified elements unless specifically stated.

It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Figure 13A:
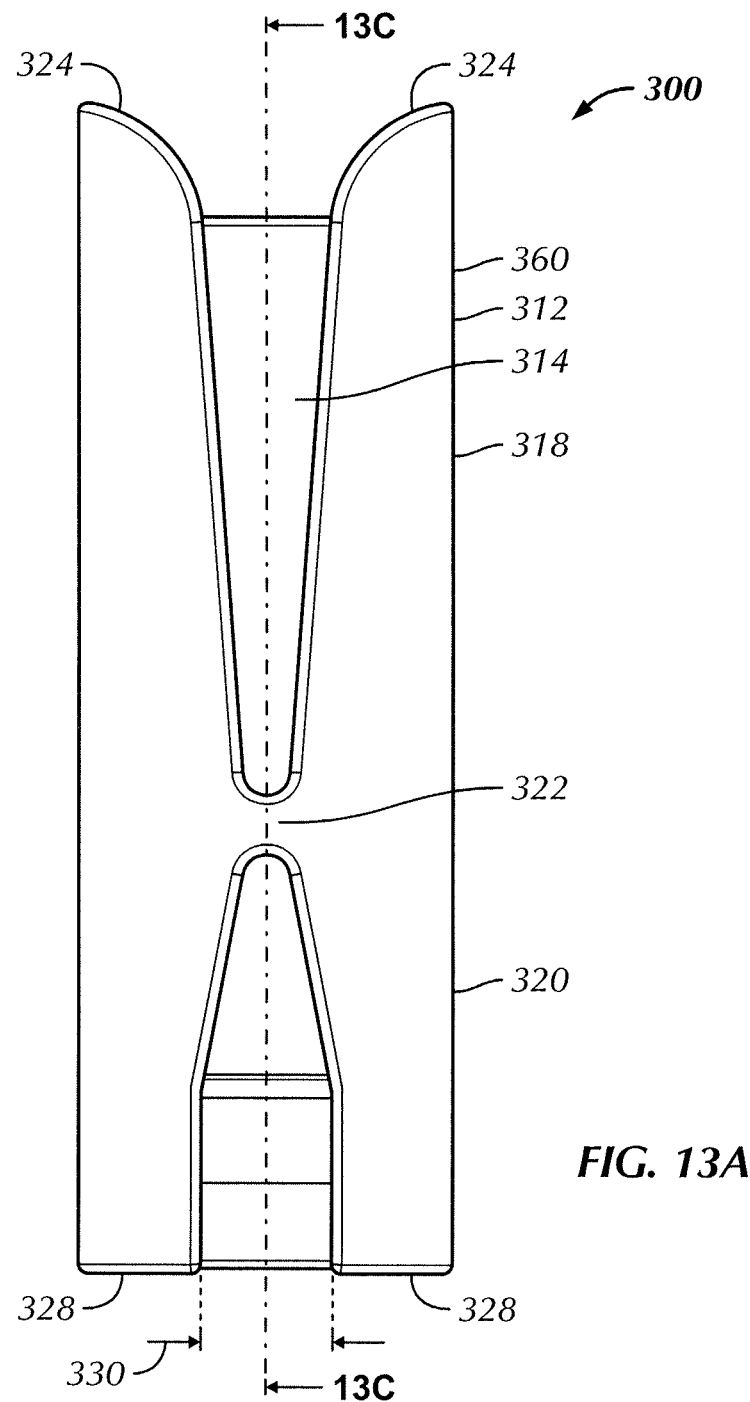
FIG. 13A is a front elevational view of a fourth embodiment of a recoil preventing needle shield.
Figure 13B:
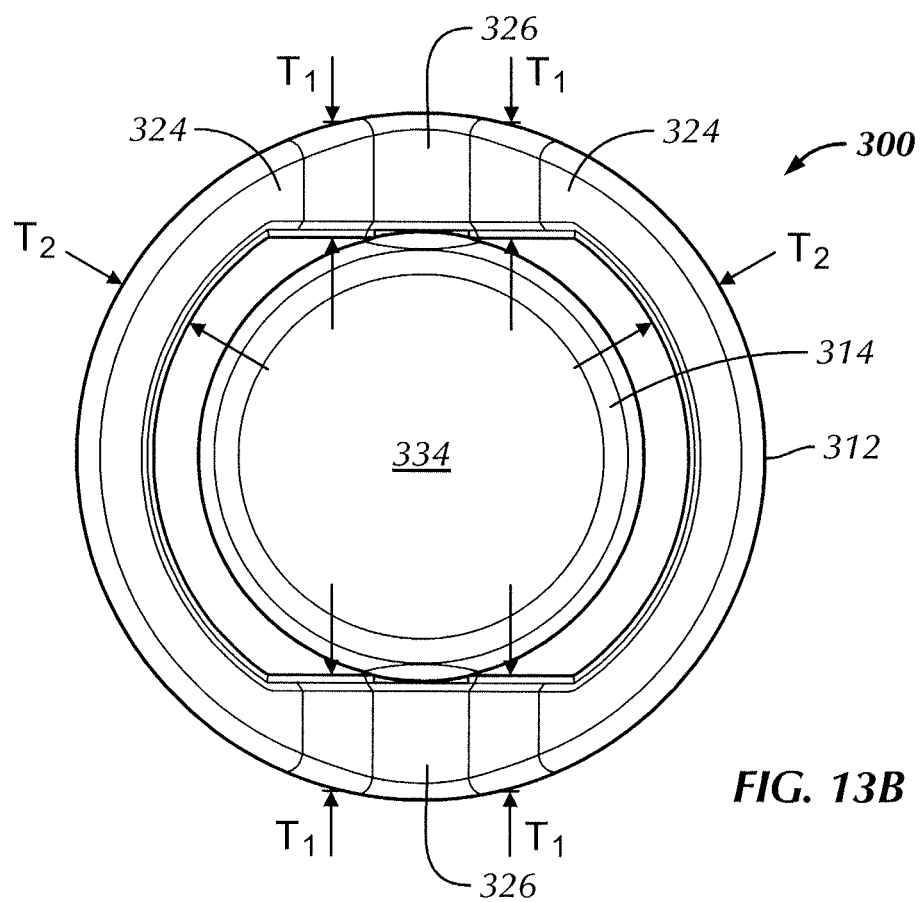
FIG. 13B is a top plan view of the needle shield of FIG. 13A.
Figure 13C:
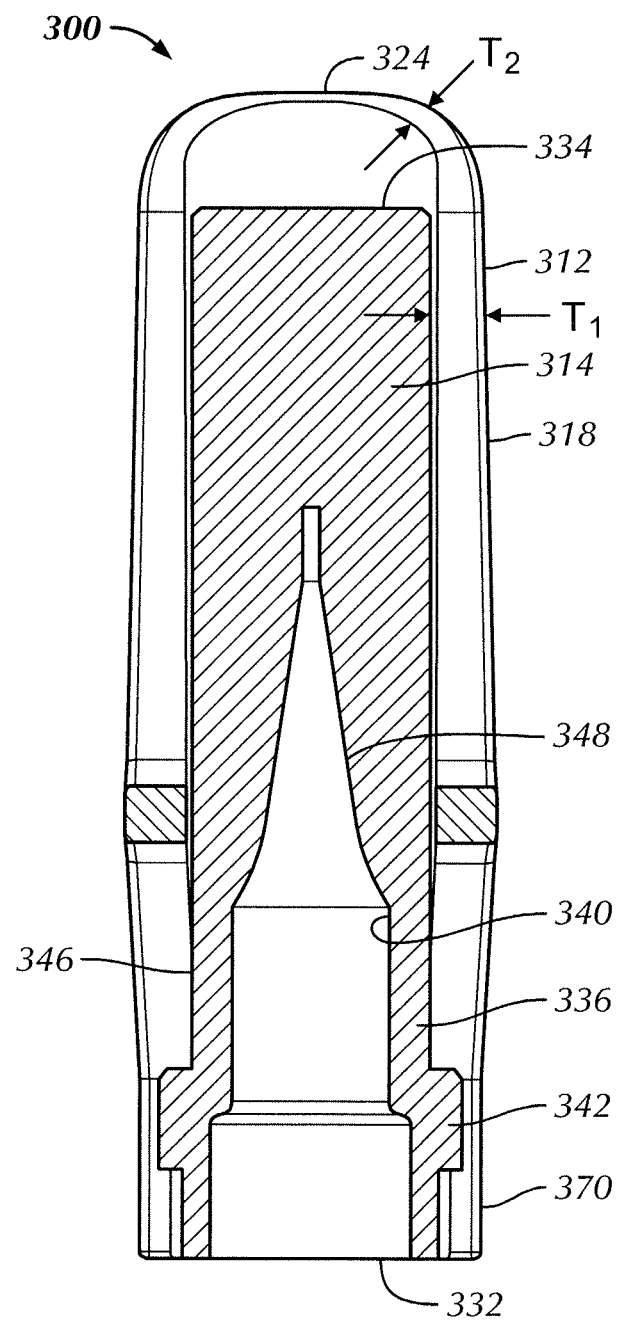
FIG. 13C is a cross-section elevational view of the needle shield of FIG. 13A, taken along section line 13C-13C.

Turning in detail to the drawings, FIGS. 1A-13C show various embodiments of recoil preventing needle shields. FIGS. 1A-5B show a first embodiment of a needle shield 10; FIGS. 6A-8B show a second embodiment of a needle shield 100; FIGS. 9A-12B show a third embodiment of a needle shield 200; and FIGS. 13A-13C show a fourth embodiment of a needle shield 300.

Figure 1B:
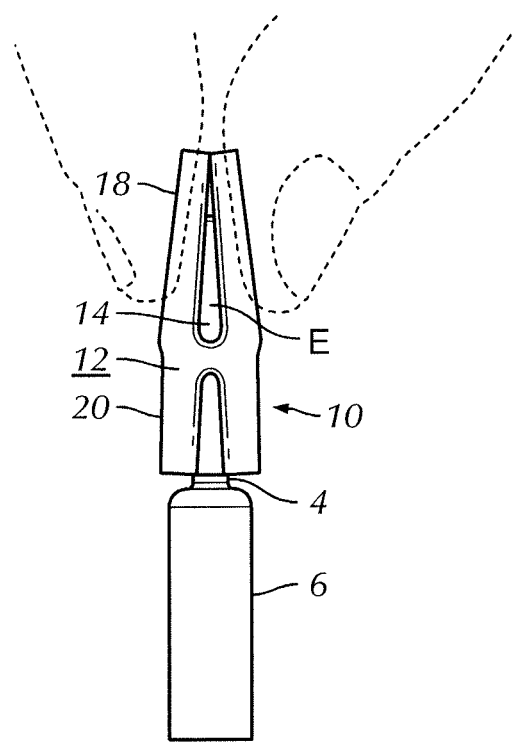
FIG. 1B is a front elevational view of the recoil preventing needle shield of FIG. 1 in a flexed state, as the needle shield is being removed from the syringe.
Figure 4A:
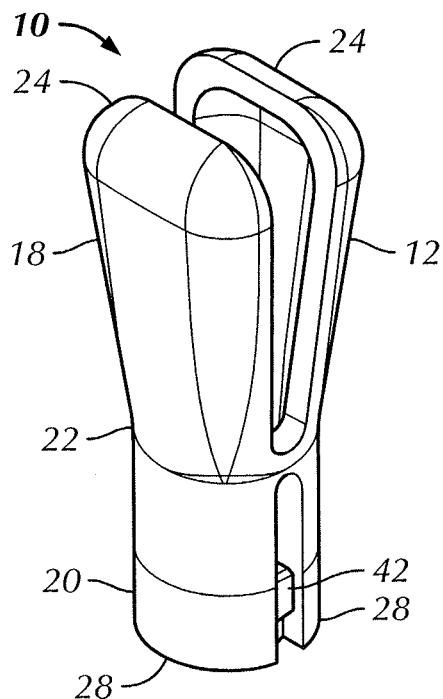
FIG. 4A is an upper front, right perspective view of the needle shield of FIG. 2A.
Figure 4B:
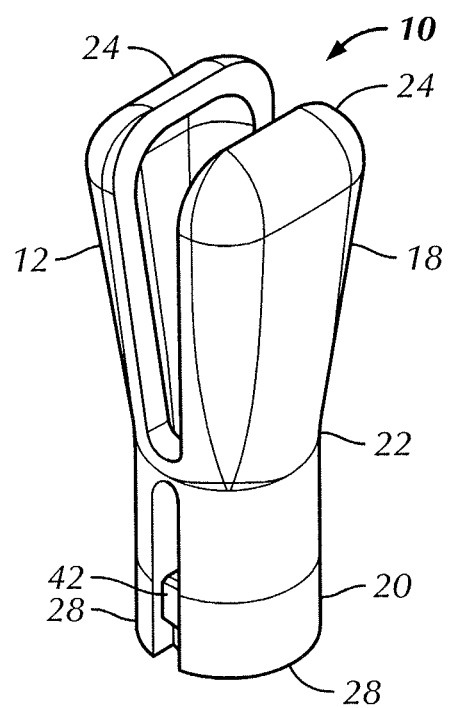
FIG. 4B is an upper front, left perspective view of the needle shield of FIG. 2A.
Figure 4C:
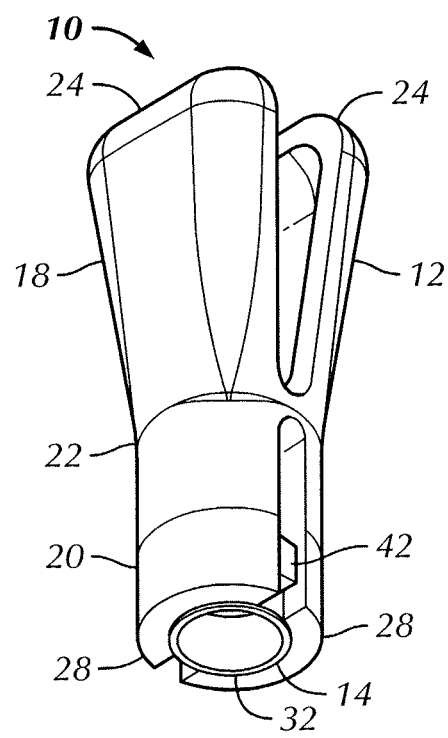
FIG. 4C is a lower front, right perspective view of the needle shield of FIG. 2A.
Figure 4D:
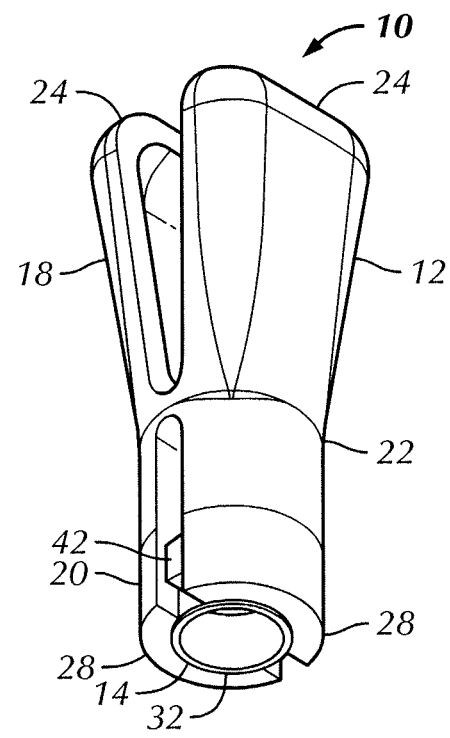
FIG. 4D is a lower front, left perspective view of the needle shield of FIG. 2A.
Figure 5A:
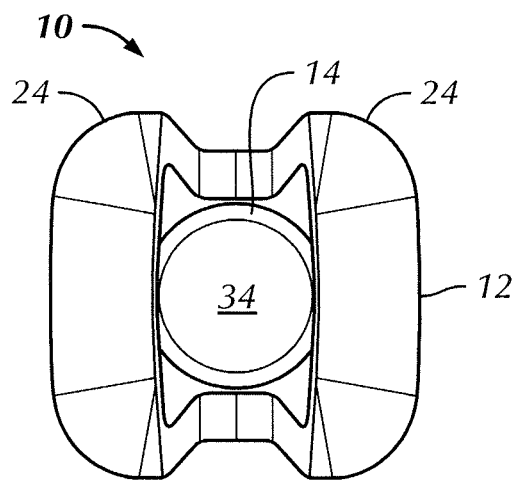
FIG. 5A is a top plan view of the needle shield of FIG. 2A.
Figure 5B:
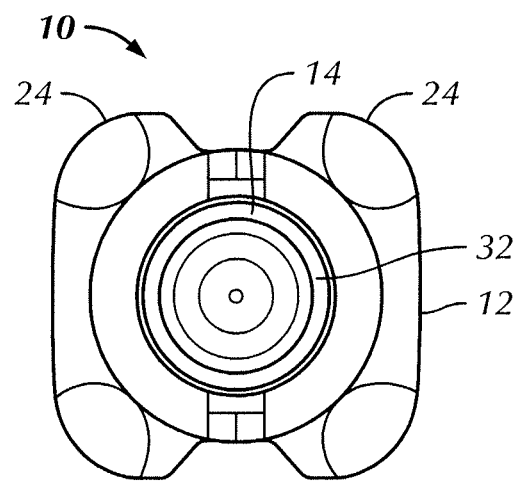
FIG. 5B is a bottom plan view of the needle shield of FIG. 2A.
Figure 8A:
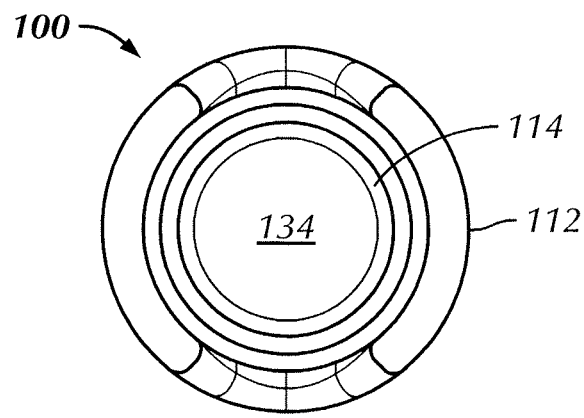
FIG. 8A is a top plan view of the needle shield of FIG. 6A.
Figure 8B:
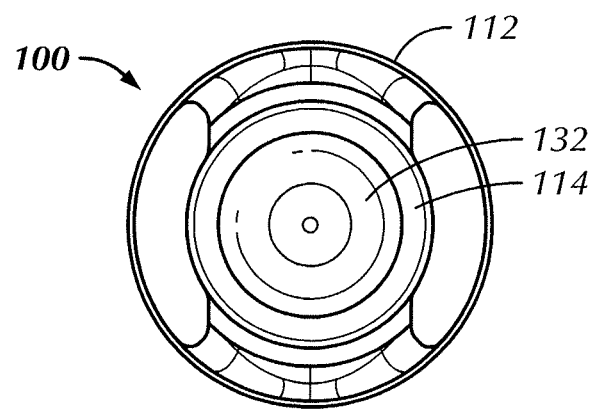
FIG. 8B is a bottom plan view of the needle shield of FIG. 6A.
Figure 9A:
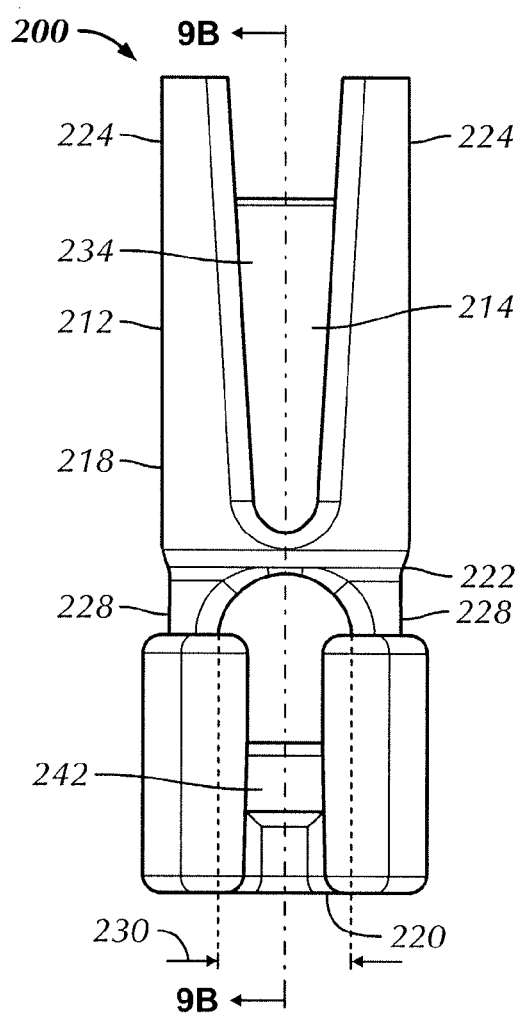
FIG. 9A is a front elevational view of a third embodiment of a recoil preventing needle shield.
Figure 9B:
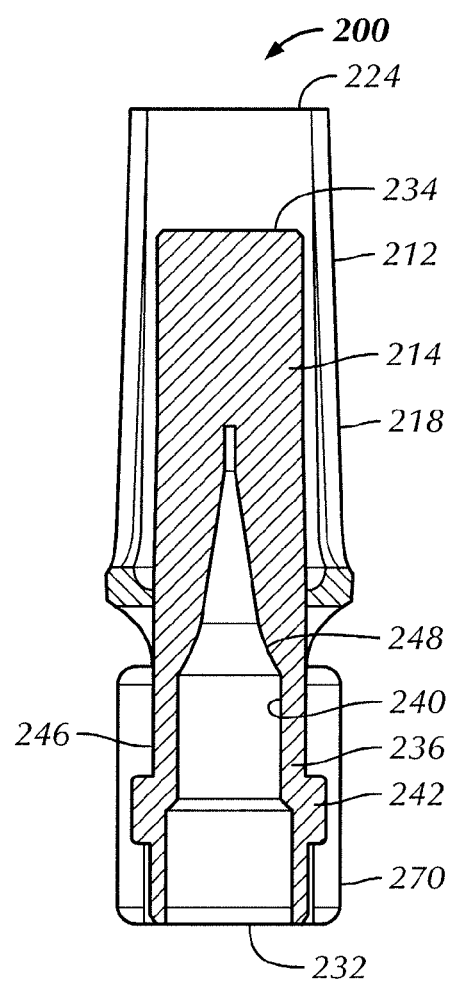
FIG. 9B is a cross-sectional elevational view of the needle shield of FIG. 9A, taken along sectional line 9B-9B.

Referring to FIGS. 1A and 1B, the needle shield 10 is shown in an initial relaxed state (FIG. 1A) and thereafter in a flexed state (FIG. 1B) after the shield 10 has been activated by a user. The needle shield 10 includes an outer shell 12 and an inner cover 14 disposed within the outer shell 12 and positioned over a needle (not shown) and at least partially over a needle hub 4. The needle is contained at least partially within the needle hub 4, which may be part of a drug container 6, for example, or other type of needle holder.

The outer shell 12 is generally divided into an upper portion 18 and a lower portion 20, having at least one flexible interface 22 (e.g. a living hinge) therebetween, which defines a fulcrum between the upper portion 18 and the lower portion 20, as will be described in further detail below. As shown in FIGS. 4A-4D, the upper portion 18 includes a plurality of upper flex members 24 extending upwardly from the flexible interface 22. In the present embodiment, two flex members 24 are shown symmetrically positioned about a central axis $\alpha_1$ such that the upper portion 18 forms a clam-like shape. As such, the upper portion 18 defines an enclosure E (FIGS. 1B, 2B) when the shield 10 has been activated by the user. As should be understood by those of ordinary skill in the art, although the upper portion 18 has two upper flex members 24 in the illustrated embodiment, forming a clam-like shape, the number of upper flex members 24 is not so limited. The upper portion 18 may include any number of upper flex members 24 such that an enclosure is formed around the inner cover 14, as particularly shown in FIG. 1B.

Preferably, when the upper portion 18 forms a clam-like shape, an upper clearance area 26 is further defined at an angle $\beta_1$ between the upper flex members 24, as particularly shown in FIG. 3B. At least one upper clearance area 26 is preferably defined at least partially between the upper flex members 24. The lower portion 20 of the outer shell 12 similarly includes a plurality of lower flex members 28 extending downwardly from the flexible interface 22, having a lower clearance area 30 defined at least partially therebetween. In contrast to the upper clearance areas 26, at least one lower clearance area 30 is disposed in the lower portion 20. When the upper flex members 24 are pinched or pressed together by a user (FIG. 1B), the lower flex members 28 pivot about the flexible interface 22, i.e., the fulcrum, and flex radially outwardly.

As best shown in FIGS. 2B and 3B, the inner cover 14 includes an open proximal end 32, a closed distal end 34, a sidewall 36 and a needle cavity 38 defined therein. The sidewall 36 extends between the open proximal end 32 and the closed distal end 34, while the needle cavity 38 preferably has an inner profile 40, which is complementary to a portion of the upper end of a drug container 6 and the needle. Above the flexible interface 22, the upper flex members 24 of the outer shell 12 are spaced apart from the sidewall 36 of the inner cover 14, to provide flex clearance from the flex members 24. Below the flexible interface 22, the outer geometry of the sidewall 36 of the inner cover 14 is substantially mated to the inner geometry of the lower flex member 28 of the outer shell 11. The inner cover 14 also preferably includes a radially outwardly extending retainer 42, positioned slightly above the open proximal end 32, coupled with a complementary retention element 44 in the outer shell 12. The retainer 42 may be used to facilitate coupling of the outer shell 12 and the inner cover 14. In preferred configurations, the outer shell 12 and the inner cover 14 are operatively coupled such that when the upper flex members 24 are pinched or pressed together by a user, both the lower flex members 28 and the open proximal end 32 of the inner cover flex radially outwardly, as shown in FIG. 1B. The lower clearance area 30 enables both the lower flex members 28 and the inner cover 14 to flex. As should be understood by those of ordinary skill in the art, the larger the clearance area 30, the greater the elongation potential of the inner cover 14, and, in turn, the more the open proximal end 32 of the inner cover 14 is capable of stretching.

Coupling between the outer shell 12, and the inner cover 14 may also be facilitated by adhesion, for example. Preferably, adhesion occurs between one or more outer surfaces 46 of the inner cover 14 and one or more inner surfaces 48 of the outer shell 12 proximate the lower end of the needle shield 10. Such adhesion may be achieved, for example, by providing an interference fit between the one or more outer surfaces 46 of the inner cover 14 and the one or more inner surfaces 48 of the outer shell 12. Alternatively, coupling may be achieved by other retention methods, including but not limited to co-injection molding, adhesives, ultrasonic welding, laser welding, pressure fitting, threading, and the like.

Referring particularly to FIGS. 1A and 1B, during use, the needle shield 10 is first positioned in a relaxed state (FIG. 1A) over a needle (not shown) and at least partially over a needle hub 4. To remove the needle shield 10 from the needle, a user activates the needle shield 10 by positioning his/her fingers on, and then pinching together, the upper portion 18 of the outer shell 12. In so doing, the user presses the upper flex members 24 together, closing the upper clearance area 26. As the user presses the upper flex members 24 together, the lower flex members 28 react and flex to spread apart, i.e., pivot out about the flexible interface 22 (fulcrum), as shown in FIG. 1B. Because the lower flex members 28 are operatively coupled to the inner cover 14, the open proximal end 32 of the inner cover 14 also stretches further open such that the initial pull off force required to remove the needle shield 10 from the drug container 6 is reduced or eliminated. As such, the needle shield 10 will not abruptly release from the needle holder portion of the drug container, thereby lessening or eliminating the phenomena of recoil, i.e., a user will no longer pull back to compensate for a spike in the initial break away force of the needle shield from the syringe.

FIGS. 6A-8B illustrate the second preferred embodiment of a needle shield 100 of the present invention. The reference numerals of the present embodiment are distinguishable from those of the earlier embodiment by a factor of one hundred (100), but otherwise indicate the same elements as indicated above, except as otherwise specified. The needle shield 100 of the present embodiment is substantially similar to that of the earlier embodiment. While certain like reference numerals may be shown in FIGS. 6A-8B, the description of certain similarities between the embodiments may be omitted herein for the sake of brevity and convenience, and, therefore, is not limiting.

As shown in FIGS. 6A-8B, the inner cover 114 is substantially the same as described with respect to the first embodiment. The outer shell 112, however, has a different configuration, including an enlarged lower clearance area 130 and substantially vertical outer shell sidewalls 160. The enlarged lower clearance area 130 reduces the amount of force that needs to be applied by a user to separate the lower flex members 128 and increases the elongation potential of the lower clearance area 130 upon activation of the needle shield 100.

The outer shell 112 is divided into an upper portion 118 and a lower portion 120, having at least one flexible interface 122 therebetween. The shell sidewalls 160 also extend upwardly from the flexible interface 122 to form a pronged upper portion 118. Referring to FIG. 6A, although two upper flex members 124 are shown symmetrically positioned about a central axis $\alpha_2$, the number of upper flex members 124 is not so limited. The upper portion 118 may include any number of upper flex members 124 such that upper portion 118 may be pinched to form an enclosure around the inner cover 114. Preferably, however, the arrangement of the upper flex members 124 is symmetrical with respect to the central axis $\alpha_2$. As such, the pronged upper portion 118 may include any even number of upper flex members 124. As with the first embodiment, the upper clearance area 126 is further defined at an angle $\beta_2$ between the upper flex members 124 as particularly shown in FIG. 6A. Moreover, the lower portion 120 of the outer shell 112 similarly includes a plurality of lower flex members 128, having the lower clearance area 130 defined at least partially therebetween. In use, the second embodiment 100 functions in the same manner as the first embodiment.

FIGS. 9A-12B illustrate the third preferred embodiment of a needle shield 200 of the present invention. The reference numerals of the present embodiment are distinguishable from those of the first embodiment by a factor of one hundred (200), but otherwise indicate the same elements as indicated above, except as otherwise specified. The needle shield 200 of the present embodiment is substantially similar to that of the earlier embodiments. While certain like reference numerals may be shown in FIGS. 9A-12B, the description of certain similarities between the embodiments may be omitted herein for the sake of brevity and convenience, and, therefore, is not limiting.

Figure 10A:
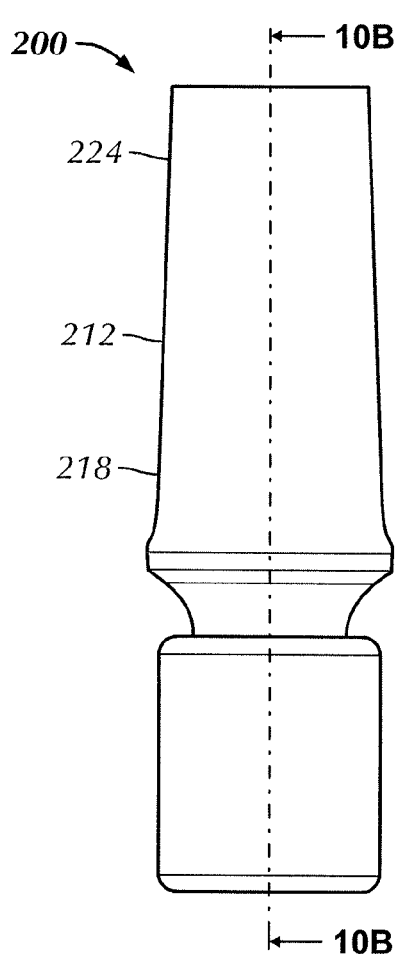
FIG. 10A is a side elevational view of the needle shield of FIG. 9A.
Figure 10B:
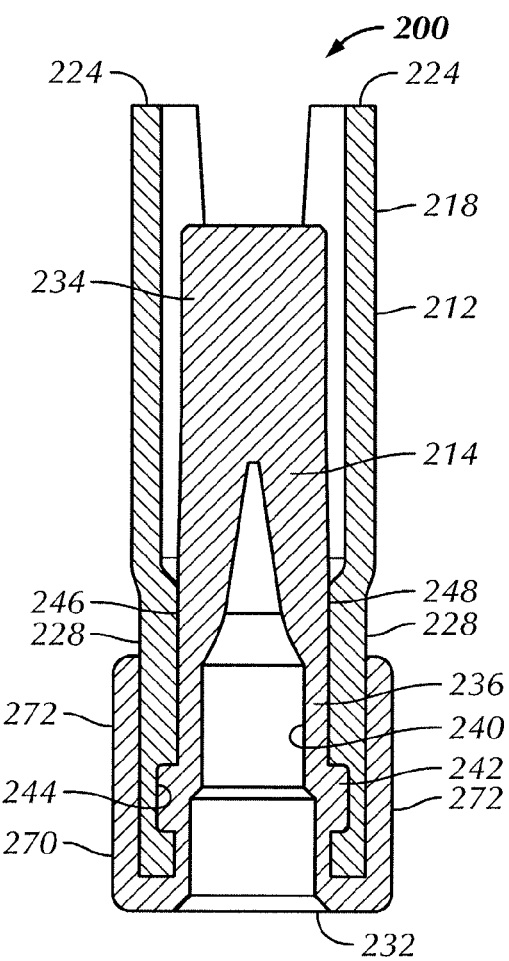
FIG. 10B is a cross-sectional elevational view of the needle shield of FIG. 9A, taken along sectional line 10B-10B of FIG. 10A.
Figure 11A:
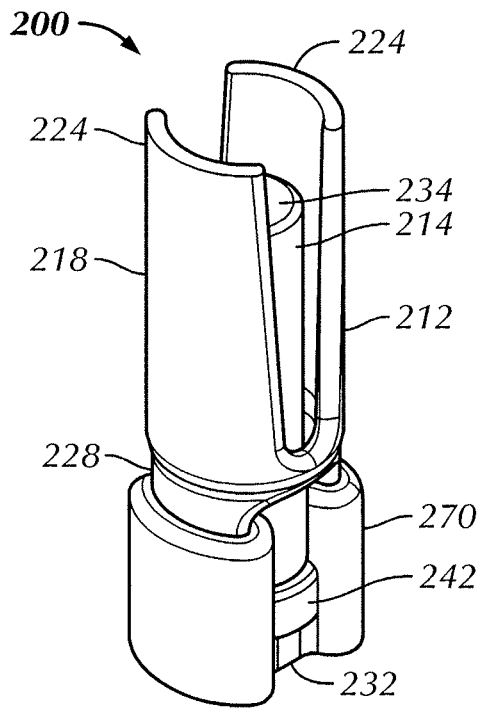
FIG. 11A is an upper front, right perspective view of the needle shield of FIG. 9A.
Figure 11B:
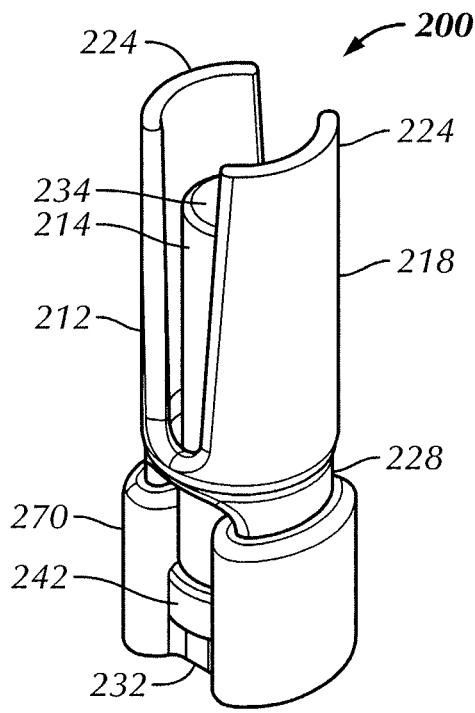
FIG. 11B is an upper front, left perspective view of the needle shield of FIG. 9A.
Figure 11C:
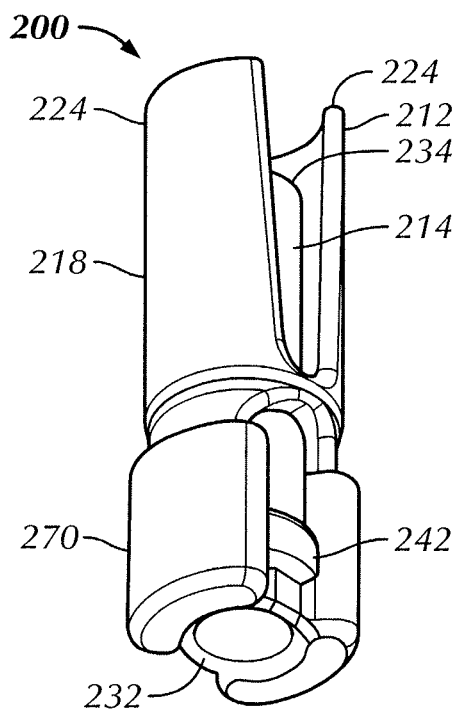
FIG. 11C is a lower front, right perspective view of the needle shield of FIG. 9A.
Figure 11D:
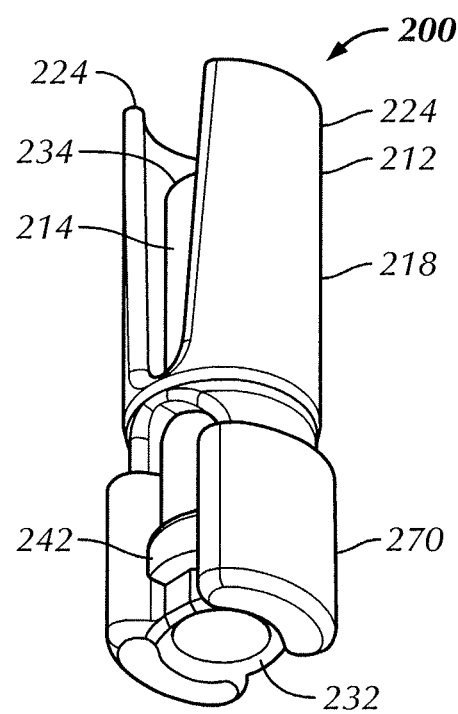
FIG. 11D is a lower front, left perspective view of the needle shield of FIG. 9A.
Figure 12A:
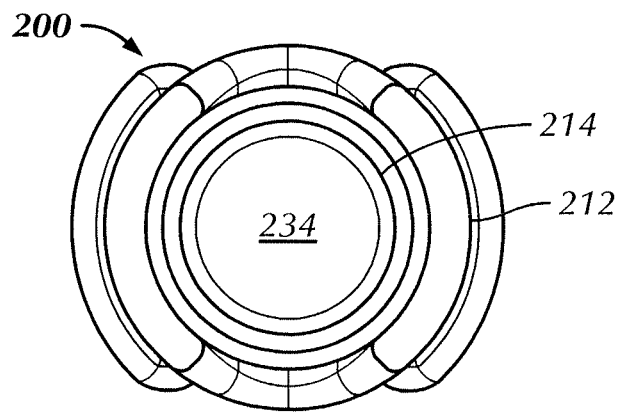
FIG. 12A is a top plan view of the needle shield of FIG. 9A.
Figure 12B:
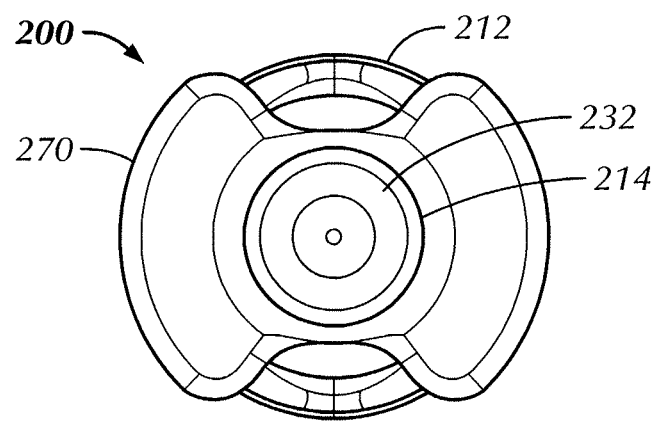
FIG. 12B is a bottom plan view of the needle shield of FIG. 9A.

In the third embodiment, the outer shell 212 is substantially similar to the outer shell 112 of the second embodiment, including a pronged upper portion 218 and an enlarged lower clearance area 230. In the third embodiment, however, the inner cover 214 has a different configuration, as best shown in FIG. 10B.

In the third embodiment of the needle shield 200, the inner cover 214 includes a coupling extension 270 integrally connected to the sidewall 236 and the retainer 242 in addition to the open proximal end 232, the closed distal end 234, and the needle cavity 238. The coupling extension 270 extends around the bottom of the outer shell 212 and upwardly to form outermost sidewalls 272. The outermost sidewalls 272 further form the lower end of the needle shield 200 and operatively connect the inner cover 214 and the outer shell 212. The inner cover 214 also preferably includes the radially outwardly extending retainer 242 positioned slightly above the open proximal end 232, coupled with the complementary retention element 244 of the outer shell 212. The retainer 242 may be used to facilitate coupling of the outer shell 212 and the inner shield cover 214. In preferred configurations, the outer shell 212 and the inner cover 214 are operatively coupled such that when the upper flex members 224 are pinched or pressed together by a user, both the lower flex members 228 and the open proximal end 232 of the inner cover will flex radially outwardly, in the manner shown in FIG. 1B. The third embodiment 200 functions in substantially the same manner as described above with respect to the first embodiment 10.

FIGS. 13A-13C illustrate the fourth preferred embodiment of a needle shield 300 of the present invention. The reference numerals of the present embodiment are distinguishable from those of the first embodiment by a factor of one hundred (300), but otherwise indicate the same elements as indicated above, except as otherwise specified. The needle shield 300 of the present embodiment is substantially similar to that of the earlier embodiments. While certain like reference numerals may be shown in FIGS. 13A-13C, the description of certain similarities between the embodiments may be omitted herein for the sake of brevity and convenience, and, therefore, is not limiting.

Similarly to the needle shield 100 of the second embodiment, the outer shell 312 of the needle shield 300 includes an enlarged lower clearance area 330 and substantially vertical outer shell sidewalls 360. The exterior profile of the outer shell 312 is generally cylindrical. As shown best in FIG. 13B, the upper flex members 324 are also substantially semi-circular in shape. In contrast to the needle shield 100, however, and as shown best in FIGS. 13B and 13C, the upper flex members 324 do not define a uniform thickness, but rather have thickened peripheral-side thicknesses $T_1$ (adjacent the upper clearance areas 326) relative to a thinner central thickness $T_2$ between the peripheries. As shown in FIG. 13B, the increase in thickness between $T_2$ and $T_1$ is added on an interior side of the upper flex members 324. That is, the exterior profile of the outer shell sidewalls 360 remains semi-circular from one periphery to the opposing periphery.

One advantage of the thickened peripheral side thicknesses $T_1$ on the interior side of the upper flex members 324 is an increase in the structural rigidity of the upper flex members 324, without increasing the overall size of the needle shield 300, i.e., the outside diameter of the needle shield 300 is not increased. Increased structural rigidity of the upper flex members 324 assists in preventing the flex members 324 from merely deforming when pinched or squeezed by a user rather than flexing as intended, i.e., pivoting about the flexible interface 322 (fulcrum), in order to stretch the lower flew members 328 radially outwardly.

In each embodiment disclosed herein, the outer shell 12, 112, 212, 312 is preferably manufactured from a polymer-based material with material properties that allow the outer shell to have a generally rigid outer surface. The polymer based material is also preferably flexible enough that the upper flex members 24, 124, 224, 324 and the lower flex members 28, 128, 228, 328 may respectively flex radially inwardly and outwardly without substantial deformation as the needle shield 10, 100, 200, 300 is being removed from the needle holder.

Moreover, in each embodiment disclosed herein, the inner cover 14, 114, 214, 314 is preferably manufactured from an elastomeric material that includes rubber or resins with similar characteristics. Preferred materials may also include material properties that enhance bonding of one or more outer surfaces of the inner cover to one or more inner surfaces of the outer shell.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A recoil reducing needle shield for covering a drug container with a needle, comprising:
    an outer shell, including an upper portion, a lower portion, and at least one flexible interface positioned therebetween, defining a fulcrum between the upper portion and the lower portion, such that radially inward flexing of the upper portion, from the flexible interface and upwardly, causes radially outward flexing of the lower portion, from the flexible interface and downwardly, about the at least one flexible interface; and
    an inner cover mounted within the outer shell, the inner cover including an open proximal end, a closed distal end, and a needle cavity defined therein for receiving a portion of the drug container including the needle, at least a portion of the inner cover being disposed within the outer shell;
    wherein the open proximal end of the inner cover is coupled to at least a portion of the lower portion of the outer shell, such that radially outward flexing of the lower portion stretches the open proximal end of the inner cover, thereby reducing an initial pull-off force required to remove the needle shield from the drug container.

2. The recoil reducing needle shield according to claim 1, wherein the upper portion of the outer shell comprises a plurality of upper flex members extending upwardly from the at least one flexible interface and having at least one upper clearance area therebetween.

3. The recoil reducing needle shield according to claim 2, wherein the plurality of upper flex members are symmetrically positioned about the at least one flexible interface.

4. The recoil reducing needle shield according to claim 1, wherein the lower portion of the outer shell comprises a plurality of lower flex members extending downwardly from the at least one flexible interface and having at least one lower clearance area therebetween.

5. The recoil reducing needle shield according to claim 1, wherein the outer shell comprises substantially vertical sidewalls.

6. The recoil reducing needle shield according to claim 1, wherein the inner cover includes a radially outwardly extending retainer and the lower portion of the outer shell includes a complementary retention element receiving the retainer therein, thereby coupling the open proximal end of the inner cover to the lower portion of the outer shell.

7. The recoil reducing needle shield according to claim 1, wherein the needle cavity of the inner cover defines an inner profile which is complementary to the portion of the drug container including the needle received in the needle cavity.

8. The recoil reducing needle shield according to claim 1, wherein the at least one flexible interface comprises a living hinge.

9. The recoil reducing needle shield according to claim 1, wherein the outer shell is comprised of a polymeric material and the inner cover is comprised of an elastomeric material.

10. A recoil reducing needle shield for covering a drug container with a needle, comprising:
    an outer shell, including an upper portion, a lower portion, and at least one flexible interface positioned therebetween, defining a fulcrum between the upper portion and the lower portion, such that radially inward flexing of the upper portion causes radially outward flexing of the lower portion about the at least one flexible interface, and the upper portion comprises a plurality of upper flex members extending upwardly from the at least one flexible interface and having at least one upper clearance area therebetween, wherein each of the plurality of upper flex members defines a substantially semi-circular exterior profile, and each of the plurality of upper flex members defines thickened peripheral sides, adjacent the at least one upper clearance area, relative to a thinner central thickness between the peripheral sides; and
    an inner cover including an open proximal end, a closed distal end, and a needle cavity defined therein for receiving a portion of the drug container including the needle, at least a portion of the inner cover being disposed within the outer shell;
    wherein the open proximal end of the inner cover is coupled to at least a portion of the lower portion of the outer shell, such that radially outward flexing of the lower portion stretches the open proximal end of the inner cover, thereby reducing an initial pull-off force required to remove the needle shield from the drug container.

11. A recoil reducing needle shield for covering a drug container with a needle, comprising:
    an outer shell, including an upper portion, a lower portion, and at least one flexible interface positioned therebetween, defining a fulcrum between the upper portion and the lower portion, such that radially inward flexing of the upper portion causes radially outward flexing of the lower portion about the at least one flexible interface; and
    an inner cover including an open proximal end, a closed distal end, and a needle cavity defined therein for receiving a portion of the drug container including the needle, at least a portion of the inner cover being disposed within the outer shell;
    wherein:

the open proximal end of the inner cover is coupled to at least a portion of the lower portion of the outer shell, such that radially outward flexing of the lower portion stretches the open proximal end of the inner cover, thereby reducing an initial pull-off force required to remove the needle shield from the drug container, and the inner cover further comprises a coupling extension extending from the open proximal end of the inner cover, around a base end of the lower portion of the outer shell and about a portion of an exterior side of the lower portion, thereby coupling the open proximal end of the inner cover to the lower portion of the outer shell.

\* \* \* \* \*